(12) United States Patent
Mullen

(10) Patent No.: US 7,229,433 B2
(45) Date of Patent: Jun. 12, 2007

(54) APPARATUS FOR TREATING PNEUMOTHORAX AND/OR HEMOTHORAX

(76) Inventor: Gary L. Mullen, 23 Cabaniss Crescent #23, Pensacola, FL (US) 32508

(*) Notice: Subject to any disclaimer, the term of this patent is extended or adjusted under 35 U.S.C. 154(b) by 248 days.

(21) Appl. No.: 10/656,245

(22) Filed: Sep. 8, 2003

(65) Prior Publication Data
US 2005/0054983 A1    Mar. 10, 2005

(51) Int. Cl.
*A61M 39/00* (2006.01)

(52) U.S. Cl. .................. 604/164.04; 604/158

(58) Field of Classification Search ........... 604/167.02, 604/167.03, 247, 257, 264, 158, 320, 122, 604/22, 164.01, 164.02, 164.06, 117, 164.04
See application file for complete search history.

(56) References Cited

U.S. PATENT DOCUMENTS

| | | | |
|---|---|---|---|
| 2,154,968 A | | 4/1939 | Alkio |
| 3,385,300 A | | 5/1968 | Holter |
| 3,459,189 A | | 8/1969 | Alley et al. |
| 3,613,684 A | | 10/1971 | Sheridan |
| 3,703,899 A | * | 11/1972 | Calinog ............... 604/264 |
| 4,153,058 A | * | 5/1979 | Nehme ............. 604/167.03 |
| 4,813,941 A | * | 3/1989 | Shea ..................... 604/247 |
| 5,078,689 A | | 1/1992 | Keller |
| 5,344,410 A | | 9/1994 | Kolkin et al. |
| 5,419,776 A | | 5/1995 | Baer |
| 5,478,333 A | | 12/1995 | Asherman, Jr. |
| 5,693,031 A | * | 12/1997 | Ryan et al. ........ 604/167.03 |
| 5,865,807 A | | 2/1999 | Blake, III |
| 5,897,531 A | | 4/1999 | Amirana |
| 6,569,121 B1 | | 5/2003 | Purow et al. |
| 2002/0010427 A1 | | 1/2002 | Scarfone et al. |
| 2003/0018309 A1 | * | 1/2003 | Breznock ................. 604/320 |
| 2003/0097119 A1 | | 5/2003 | Garabedian et al. |

FOREIGN PATENT DOCUMENTS

| | | | |
|---|---|---|---|
| DE | 3421170 | | 12/1985 |
| EP | 0853953 | | 7/1998 |
| WO | WO 95/18642 | * | 1/1994 |
| WO | WO 95/18642 | | 7/1995 |

* cited by examiner

*Primary Examiner*—Nicholas D. Lucchesi
*Assistant Examiner*—Melissa A. McCorkle
(74) *Attorney, Agent, or Firm*—Black Lowe & Graham PLLC

(57) ABSTRACT

An apparatus for treating pneumothorax and/or hemothorax that does not require the assembly of parts and can be used by medical personnel with minimal experience and training in treating these conditions. The apparatus comprises a trocar obturator unit comprising a stylet having a point for puncturing the chest or other body cavity, and a stopper integrally attached to the stylet. The catheter assembly is comprised of a tube dimensioned to receive the stylet and a hub integrally attached to the distal end of the catheter assembly for receiving the stopper. The one-way valve composed of a pliable material covers the hub. The lumen of the one-way valve is continuous with the lumens of the tube and the hub of the catheter assembly. The trocar obturator unit also includes a pull handle for safely removing the trocar obturator unit from the catheter assembly in accordance with the method of the invention.

49 Claims, 9 Drawing Sheets

APPARATUS FOR TREATING PNEUMOTHORAX AND/OR HEMOTHORAX

BACKGROUND OF THE INVENTION

1. Field of the Invention

The present invention relates to a device for treating patients suffering from a pneumothorax, tension pneumothorax, and/or hemothorax. The device is particularly unique in that it is does not require the assembly of parts and can be used by medical personnel with minimal experience and training in treating these conditions, and without additional supplies or instrumentation.

2. Description of the Related Art

Normally, the pressure in the lungs is greater than the pressure in the pleural space surrounding the lungs. However, collection of air the pleural space causes a loss of the negative pressure that causes the lung to collapse partially or completely. This condition is known generally as a pneumothorax. There are various types of pneumothorax including spontaneous pneumothorax, traumatic pneumothorax, and tension pneumothorax (synonymous with pressure pneumothorax or valve pneumothorax). Spontaneous pneumothorax exists in two forms, namely, simple spontaneous pneumothorax and complicated spontaneous pneumothorax. Simple spontaneous pneumothorax typically occurs suddenly or for no known reason. It is caused by rupture of a small air sac or fluid-filled sac in the lung, and most frequently strikes tall, thin men between the ages of 20 to 40. People with lung disorders, such as emphysema, cystic fibrosis, and tuberculosis, are at higher risk for spontaneous pneumothorax. Complicated spontaneous pneumothorax, also generally caused by rupture of a small sac in the lung, occurs in people with pre-existing lung diseases. The symptoms of complicated spontaneous pneumothorax, however, tend to be worse than those of simple spontaneous pneumothorax, due to the underlying lung disease. Spontaneous pneumothorax is characterized by dull, sharp, or stabbing chest pain that begins suddenly and becomes worse with deep breathing or coughing. Other symptoms include dyspnea, tachypnea, and cough.

Traumatic pneumothorax occurs as the result of accident or injury, either iatrogenic due to medical procedures performed to the chest cavity, such as thoracentesis or mechanical ventilation, or following chest trauma and resultant disruption of pleural integrity. Mechanical ventilation as it is used to treat adults and neonates with respiratory distress, is often performed at pressures greater than one atmosphere. Occasionally, barotrauma from this increased pressure results in lung disruption. Following chest trauma or lung barotrauma, air may enter the chest cavity via the damaged lung parenchyma, or through a defect in the chest wall, causing the lung to collapse.

When the abnormal accumulation of air in the pleural space is at a pressure greater than the ambient pressure, the pneumothorax is termed a tension pneumothorax. A tension pneumothorax is often the immediate result of an injury, the delayed complication of a hidden injury, such as a fractured rib, that punctures the lung; or the result of lung damage from asthma, chronic bronchitis, or emphysema. A physiologic one-way valve (secondary to damage in the lung parenchyma) allows air to enter the chest cavity, and become trapped. As inspiration becomes more difficult, the patient inspires with more force, or coughs thereby increasing his intrathoracic pressure, and air continues to be forced into the tension pneumothorax. As the pressure further increases, the mediastinal structures shift toward the contralateral chest, thereby decreasing venous return to the heart, and decreasing the ability of the heart muscle to fill during diastole. Due to this displacement, neither lung is able to properly inflate, and this cardiovascular and cardiorespiratory embarrassment is rapidly fatal if the tension pneumothorax is not promptly vented. The patient appears distressed, dyspneic, cyanotic, tachypneic and tachycardic. Distended neck veins, and a tracheal shift to the contralateral side are also key clinical signs. Early diagnosis is critical for patient survival. In-hospital patients who are being ventilated with positive pressure mechanical ventilation are often sufferers of occult tension pneumothorax, which develops exceedingly rapidly due to the high pressures used to mechanically ventilate them. Early diagnosis in this group of patients and prompt treatment is also critical for survival.

Hemothorax is the collection of blood in the thoracic cavity. It occurs when chest trauma is significant enough to damage any of the vascular structures in the thorax. As the thoracic cavity fills with blood, the lung has a decreased ability to expand normally, thereby decreasing oxygenation and ventilation. If a hemothorax continues to worsen, death may occur by exsanguination or hypoxia. Patients with large hemothorax may demonstrate signs of shock, and decreased neck vein distention. In patients with a combination of tension pneumothorax and hemothorax, death may occur due to any of the mentioned physiologic changes. In-hospital treatment of a hemothorax is similar to that of a pneumothorax and is accomplished by use of closed thoracostomy via a water-seal chest tube drainage device. Additionally, surgical intervention may be necessary to control the cause of the bleeding.

There are various known devices for treating these conditions. For example, U.S. Pat. No. 3,613,684 to Sheridan discloses a trocar catheter designed for the emergency treatment of a pneumothorax. A particularly disadvantageous feature of this device however, is that prior to using the device, a surgeon or other medical personnel must make an incision in the skin of the patient using a separate scalpel or knife. Further, the device provides an open communication between the chest cavity and the outside atmosphere. This device also requires a closed underwater seal system or other auxiliary equipment for proper operation. Given the urgency required in the treatment of a tension pneumothorax, the time required to retrieve and sterilize the scalpel and to make the incision prior to the insertion of this device and to connect the catheter to an auxiliary system could very well prove to be fatal. Moreover, because the medical personnel treating the patient is required to carry additional instrumentation in order to employ the device, the device is not well suited for pre-hospital use, use on battlefields, or other areas of mass casualty where storage and access to additional, sterilized medical instruments is extremely limited.

U.S. Pat. No. 4,153,058 to Nehme discloses a pleural decompression catheter for releasing entrapped air within a human body. The device consists of an elongated member axially insertable into a human body and having a fluid passage means for establishing fluid communication from the exterior of the elongated member to one end of the member positioned exteriorly of the body. A one-way valve is coupled to the exteriorly extending end of the elongated member. The one-way valve consists of a balloon which is attached to a relatively large exterior housing. Once the catheter is inserted into the patient, the trocar is removed in release the entrapped air within the chest cavity. The size and complexity of this device, however, renders this device ill-suited for use in emergency situations. Moreover, this device provides no means for affixing the device to the patient to ensure that the catheter is not prematurely removed from the patient when the patient is transported, or otherwise. In addition, as there is no means for securing the device to the patient, one is required to hold the exterior housing against the patient's chest so that the catheter does not shift or become disengaged. Additionally, the rigid nature of the external housing makes the device cumbersome if used in a pre-hospital setting, as warming blankets of the patient's garments would tend to dislodge the device. This precludes medical personnel from further tending to the patient and treating others.

U.S. Pat. No. 5,478,333 to Asherman, Jr. discloses a medical dressing for treatment of open chest injuries. The dressing consists of a discoid shaped dressing made of pliable plastic, having a central valve that extends away from the body when the device is employed. The disk has a skin adhesive on the side that is placed to the chest. The device is designed for pre-hospital use, however it is incapable of treating a tension pneumothorax in the absence of an open chest wound, as the device has no means to penetrate the chest and allow the tension pneumothorax to vent. Additionally, if used in conjunction with an intravenous catheter there is a threefold disadvantage in that (a) the catheter when inserted would cause a pneumothorax if one did not already exist, (b) the intravenous catheter when it is placed in the chest becomes a portal for contaminating the pleural cavity (especially in a chemical, biological, or radiologic battlefield environment), and (c) it would require assembly of parts and use of valuable time.

U.S. Pat. No. 5,344,410 to Kolkin et al., discloses a tubular rubber device for the drainage of pleural fluid. The device consists of a valve and plural fluid collection unit temporarily affixed to a stylet or mandrin that is inserted into the chest cavity. When the mandrin is removed, the rubber valve and collection assembly is removed. The device is not well suited for the pre-hospital treatment of tension pneumothorax because it is relatively large, and by its insertion through the chest wall causes a correspondingly large amount of tissue damage. Additionally, there is no easy way to affix the device to the skin of a patient once it has been employed. Further, the device requires that a scalpel be used to make the skin incision prior to its use, requiring medical personnel to carry additional instrumentation if they wish to use the device.

There is a need for a device that can be safely used by less experienced medical personnel, including first responders, to quickly and easily treat patients suffering from pneumothorax, tension pneumothorax, and/or hemothorax on battlefields, conditions of mass casualty, conditions of environmental chemical, biologic, or radiologic contamination, as well as in more conventional settings, such as within ambulances and hospitals.

SUMMARY OF THE INVENTION

A primary object of the present invention is to provide a device for quickly and easily treating a patient suffering from a pneumothorax, tension pneumothorax, and/or hemothorax that can be used by first respondent emergency personnel having minimal experience and training in treating these conditions.

Another object of the invention is to provide a device for quickly and easily treating a hospitalized patient who is diagnosed as having a tension pneumothorax until the patient is stabilized and can have a water-seal closed thoracostomy tube placed.

Another object of the invention is to provide a device by which first respondent emergency personnel with minimal training, or hospital personnel can effectively treat a pneumothorax, tension pneumothorax, and/or hemothorax, but which will not cause pneumothorax if employed on a patient who was misdiagnosed as having a pneumothorax, tension pneumothorax, and/or hemothorax. This is accomplished because in the chest of an individual that does not suffer from a tension pneumothorax, there is normally a negative pressure in the potential space between the parietal and visceral lung pleura. This potential space is termed the pleural space. If this space is allowed to communicate with the outside of the body, air will rush into that potential space and create a pneumothorax. A common pre-hospital treatment modality for tension pneumothorax involves inserting a 14 gauge intravenous catheter through the chest wall. However, if a patient was misdiagnosed with a tension pneumothorax by the pre-hospital personnel, then that patient would now have a pneumothorax because the lumen of the intravenous catheter would communicate with the outside air and allow that air into the pleural space. As the device of the present invention is employed on a patient and the trocar obturator is removed, the one-way valve prevents all air, other fluids, and outside contaminants from flowing in a retrograde fashion into the pleural cavity. Therefore it is not possible for the ambient air to enter and cause a pneumothorax.

Another object of the invention is to provide a pneumothorax and/or hemothorax treatment device that requires no assembly of parts prior to its use in treating pneumothorax and/or hemothorax conditions.

Another object of the invention is to provide a pneumothorax and/or hemothorax treatment device that can be quickly and easily affixed to a patient, so as to free the hands of medical personnel treating the condition.

Another object of the invention is to provide a pneumothorax and/or hemothorax treatment device that is particularly advantageous in treating these conditions in the battlefield or in conditions of mass casualty.

Another object of the invention is to provide a pneumothorax and/or hemothorax treatment device that because of its one-way valve design minimizes or prevents chemical, biological, and radiological contamination into the chest cavity when used in battlefield or warfighting situations.

Another object of the invention is to provide a sterile pneumothorax and/or hemothorax treatment device that can be efficiently packaged and stored or carried.

Another object of the invention is to provide a pneumothorax, tension pneumothorax, pneumohemothorax treatment device which has a lumen that will not kink during patient transport, thereby preventing occult tension pneumothorax.

These and other objects of the invention are achieved by providing a pneumothorax and/or hemothorax treatment device having trocar obturator unit, a catheter assembly, and a one-way valve. In a preferred embodiment, the trocar obturator is a single unit, made of a high-strength plastic, polymer, or metal, having a proximal and distal end. The trocar obturator unit consists of a solid needle stylet, a stopper, and the pull-handle. The proximal end of the stylet has a point and is particularly designed for quickly and accurately puncturing the chest or other body cavity of a patient. In a preferred embodiment, the trocar consists of a solid needle stylet, with a cylindrically-shaped stopper integrally attached to the distal end of the stylet, and a pull-string having a handle at its free-end is attached to the distal aspect of the stopper. In another preferred embodiment, the stopper is a sphere-shaped component integrally attached to the stylet. The stopper is preferably lubricated to facilitate its removal from the one-way valve during operation of the device, as disk used herein.

In its assembled form prior to use, the trocar obturator unit is removably retained in the catheter assembly. The catheter tube is, therefore, particularly designed and dimensioned to receive and house the stylet. The catheter is comprised of two main parts: a primary tube designed to receive the stylet, and a hub for, inter alia, maintaining the position of the stylet in the catheter and allowing the stopper of the trocar obturator unit to seat. The hub is integrally attached to the catheter tube, such that the lumens of the tube and the hub are continuous. The hub is preferably large enough to receive at least a portion of the stopper. In another preferred embodiment, the hub is preferably large enough to receive at least a portion of the stopper of the stylet. The length of the catheter tube is such that the point of the stylet protrudes out of and beyond the distal end of the catheter tube when the trocar obturator unit is seated on the catheter hub.

In a preferred embodiment, the catheter tube is composed of a coiled monofilament polymer or stainless steel wire, the coil of which is coated with a biologically inert plastic or similar material providing the catheter tube with an airtight lumen. This "coiled-spring" design prevents the catheter member from kinking when bent in a tight radius. Another preferred catheter tube embodiment consisting of any type of medical grade catheter material familiar to those in the trade which is designed to be bent in a tight radius without kinking could be employed.

One end of the one-way valve is attached in an airtight fashion to the catheter hub and covers at least a portion of the hub and the trocar obturator when the stylet is positioned within the catheter tube. The lumen of the one-way valve is continuous with the lumen of the catheter tube and the catheter hub. Moreover, in a preferred embodiment, the handle attached to the cylindrical deformity of the trocar obturator extends through the lumen of the one-way valve, with at least a portion of the handle protruding therefrom, such that the handle can be used to remove the trocar obturator assembly from the catheter assembly, through the lumen of the one-way valve in accordance with the method of the present invention.

In another preferred embodiment, the one-way valve is tightly secured to the hub by a collar positioned within a recess formed within the sidewall of the hub. Securing the collar to the hub ensures that the one-way valve is not unintentionally removed when the trocar obturator assembly is removed through the one-way valve, and ensures that the one-way valve forms an airtight seal with the catheter hub. Another preferred means of securing the one-way valve to the hub is with a permanent adhesive that is capable of being sterilized.

In yet another embodiment of the present invention, provided is at least one means for securing the trocar catheter to the patient, so as to permit the practitioner treating the pneumothorax or hemothorax to use his/her hands for additional tasks or to simultaneously treat multiple patients. A preferred securing means is at least one band attached to the catheter hub, the free end of which is attached a tab having adhesive coating such as 3M™ Acrylate Polymer® or other similar type skin adhesive on at least one end, for securing the adhesive band to the patient. Prior to use, the band can be stored in the recess on the hub. To protect the adhesive coating on the tabs prior to use, the adhesive bands are preferably covered by a removable covering which does not affect the integrity of the adhesive when removed.

Another preferred means for securing the trocar unit to a patient consists of a disk integrally positioned on the proximal side of the catheter hub. The disk is fabricated from thin, flexible polyethylene (as an example 3M™ polyethylene film). The disk has a central opening through which the catheter tube extends, and is integrally fastened to the catheter hub. The underside (proximal side) of the disk is preferably coated with a skin adhesive such as 3M™ Acrylate Polymer® or other similar type skin adhesive so that the disk can be adhesively attached to the patient. Prior to use, the adhesive side of the disk is preferably coated by a removable covering which does not affect the integrity of the adhesive when removed. Alternatively, the disk can be stapled to the patient in accordance with methods known to those of ordinary skill.

In yet another preferred embodiment, at least the trocar obturator, and the catheter tube are composed of a radio-opaque material, or contain radio-opaque markers.

DETAILED DESCRIPTION OF THE INVENTION

Figure 1:
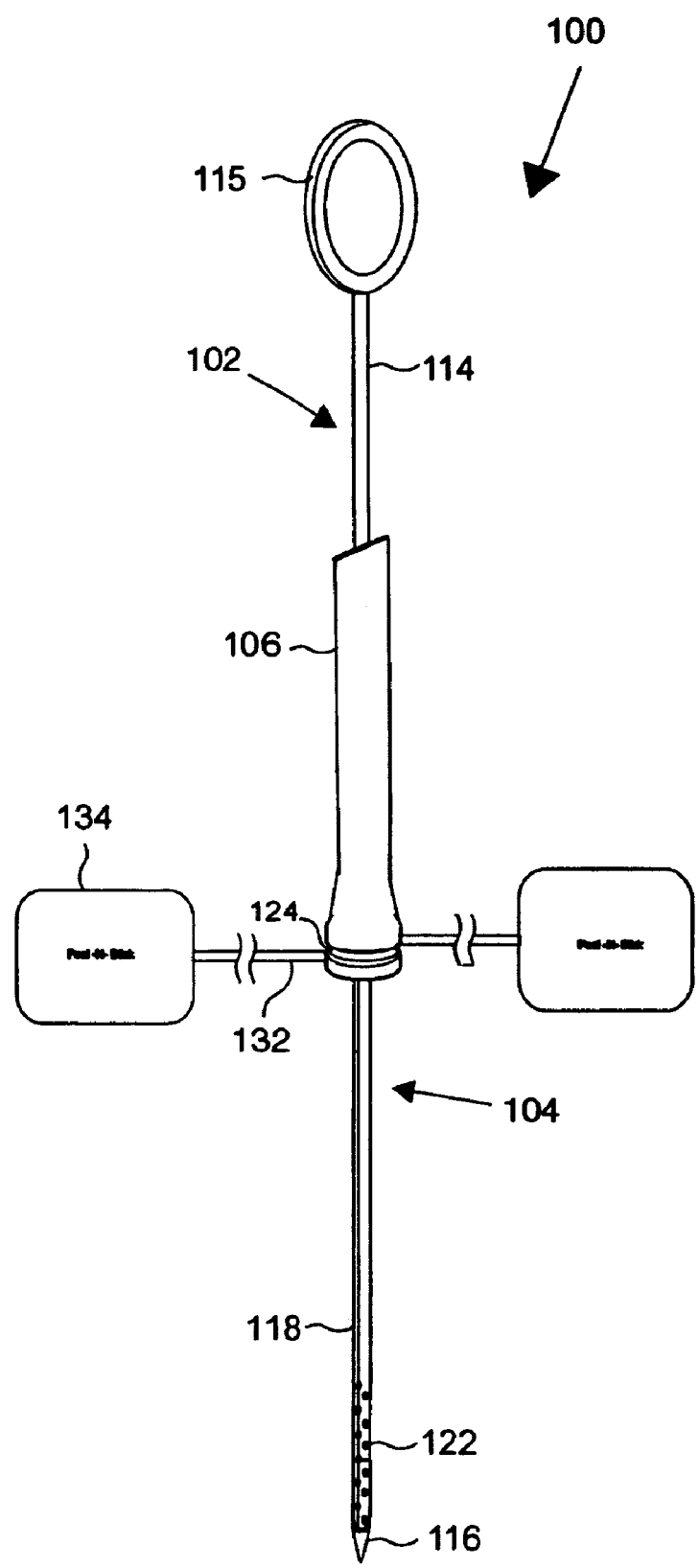
FIG. 1 is a isometric view of a preferred embodiment of the pneumothorax and/or hemothorax treatment device of the present invention, as assembled prior to use with tabs as the attachment means.

Referring to FIG. 1, illustrates a preferred embodiment of the pneumothorax and/or hemothorax treatment device 100 of present invention as assembled and ready for use. As shown, device 100 is comprised generally of a trocar obturator unit 102, a catheter assembly 104, and a one-way valve 106, and a means 134 for attaching device 100 to a patient.

Figure 2A:
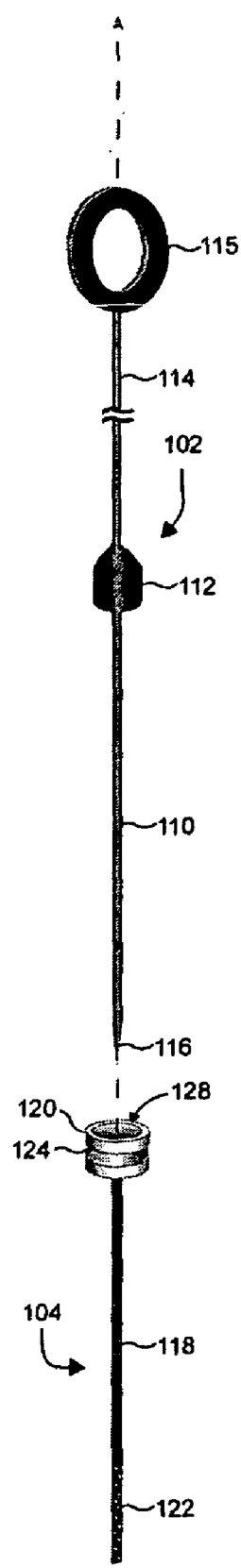
FIG. 2A is a isometric view of the trocar obturator unit and catheter assembly in accordance with one preferred embodiment of the present invention, shown separated from each other.

Referring to FIG. 2A, trocar obturator unit 102 consists of a stylet 110, an integrally coupled stopper 112, and a pull-handle 114 integrally attached to stopper 112. Stylet 110, which is preferably composed of a solid, elongated cylindrical rod composed of medical grade stainless steel or of a plastic polymer, tapers to a point 116 for penetrating through the skin, connective tissue, and muscle of a patient and into the affected pleural cavity or other body cavity.

Catheter assembly 104 consists of a hollow, elongated tube 118 having a hub 120 on its distal end. Tube 118 is fabricated from currently available medical-grade, high flexibility, kink-resistant tubing familiar to those of ordinary skill and contains a plurality of apertures 122 that extend through the wall of tube 118 at its proximal end. Hub 120 is cylindrically-shaped with a central opening that is co-extensive with and of approximately the same diameter as the interior opening of catheter tube 118. A recess 124 is centrally located on the sidewall of hub 120. In a preferred embodiment, tube 118 is composed of a tightly wound coil of a monofilament polymer, or a tightly would coil of a stainless steel wire, such that the internal lumen diameter closely approximates the outside diameter of the stylet. This "screen-door-spring" coil is then coated with a material in order to form an airtight and low friction surface to the catheter tube. Alternatively, tube 118 can be constructed of medical grade, high flexibility, kink-resistant tubing. During manufacture, catheter tube 118 is integrally affixed to catheter hub 120 by similar method of currently produced intravenous catheters.

Figure 2B:
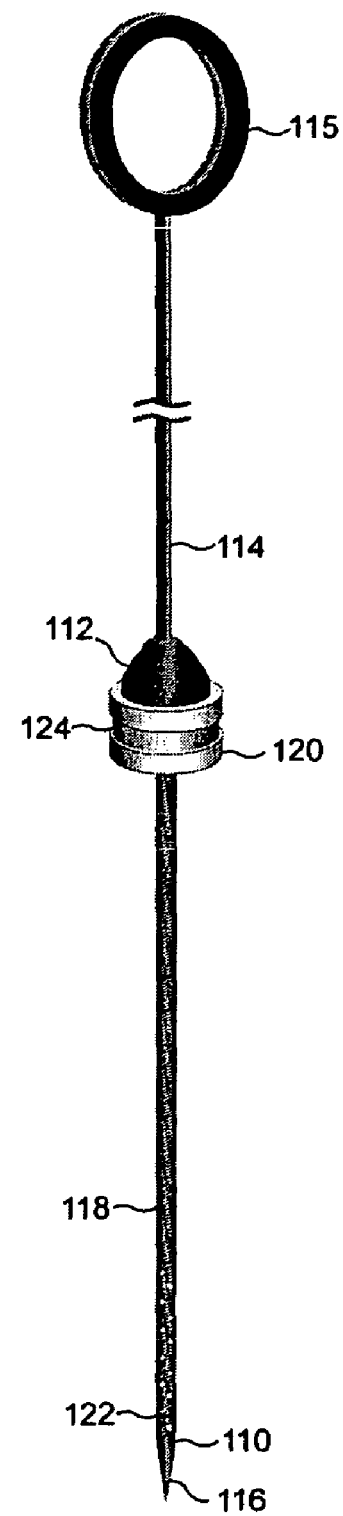
FIG. 2B is isometric views of the trocar obturator unit and catheter assembly in accordance with a one embodiment of the present invention, shown as assembled.
Figure 2C:
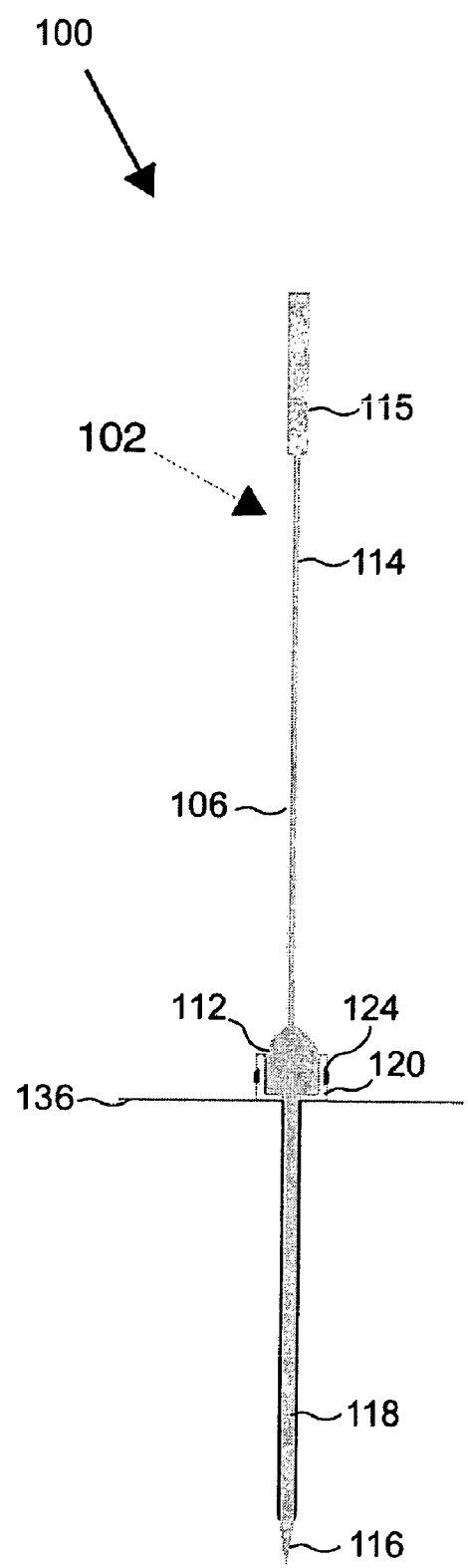
FIG. 2C is a cross-sectional side view of the pneumothorax and/or hemothorax treatment device of the present invention in accordance with one embodiment of the present invention, shown as assembled.
Figure 3:
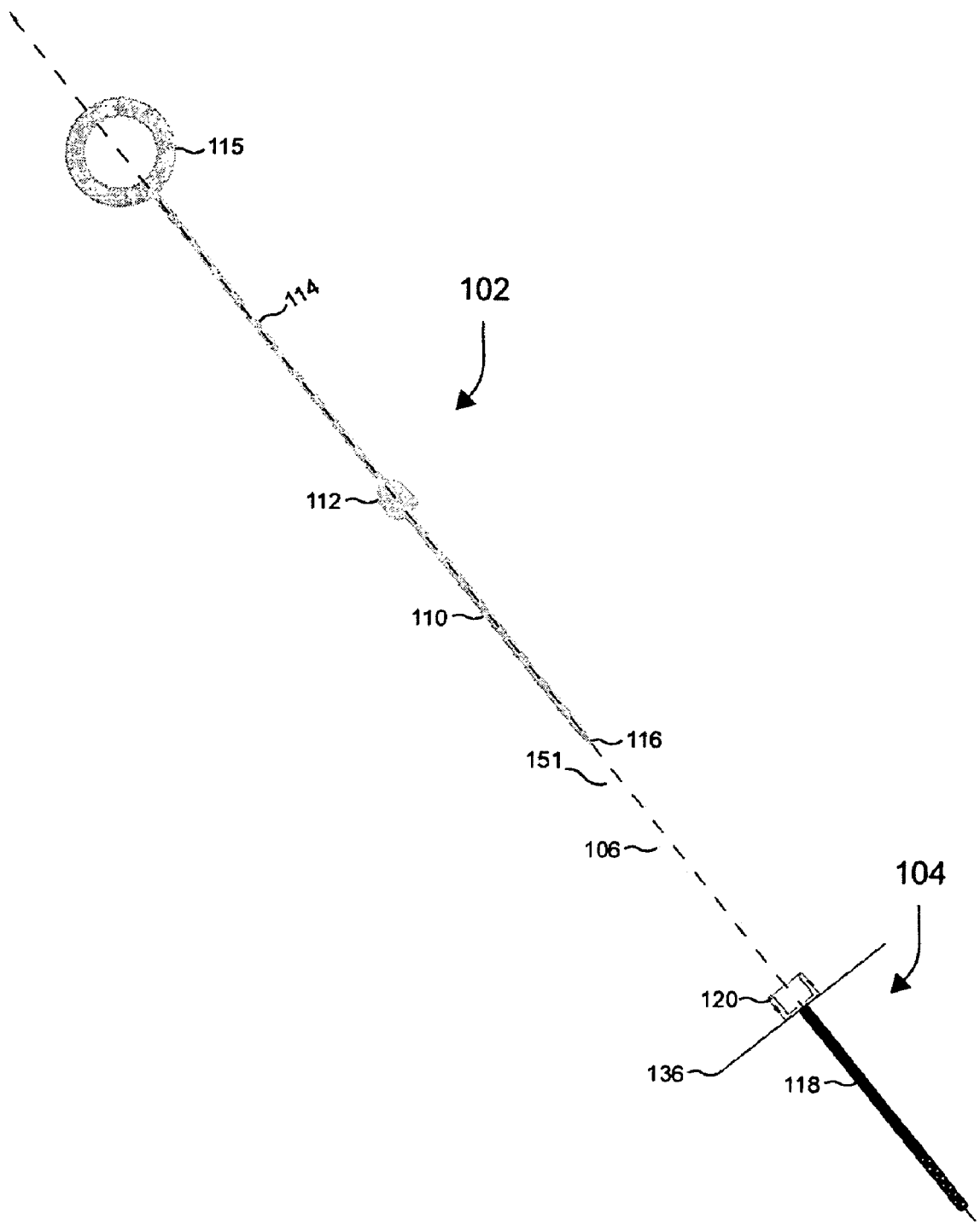
FIG. 3 is a plan view of the trocar obturator unit and catheter assembly in accordance with another embodiment of the present invention, shown separated from each other.
Figure 3A:
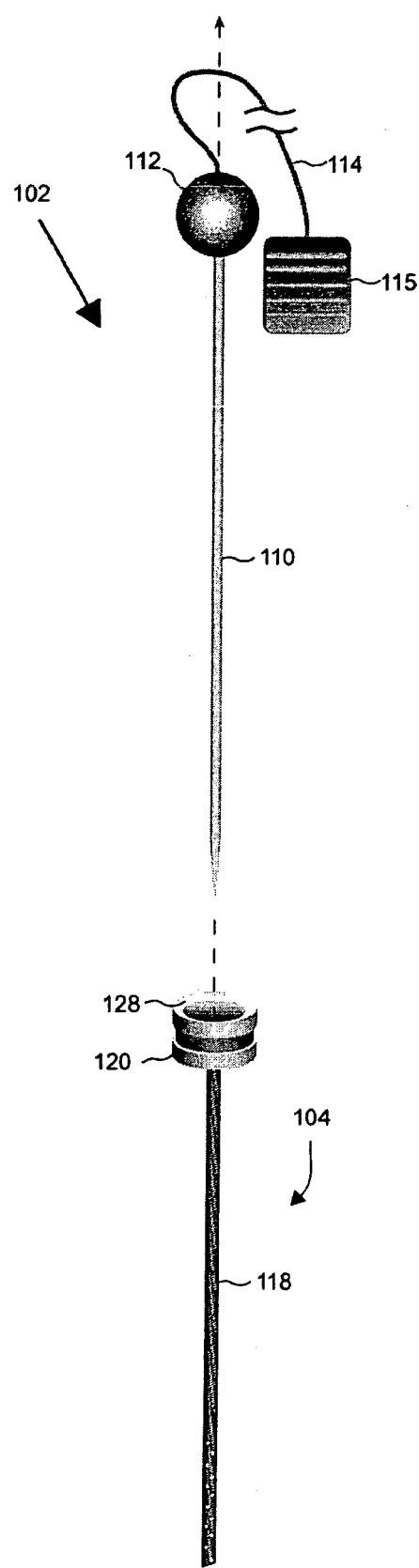
FIG. 3A is a isometric view of the trocar obturator unit and catheter assembly in accordance with another embodiment of the present invention, shown separated from each other.
Figure 3B:
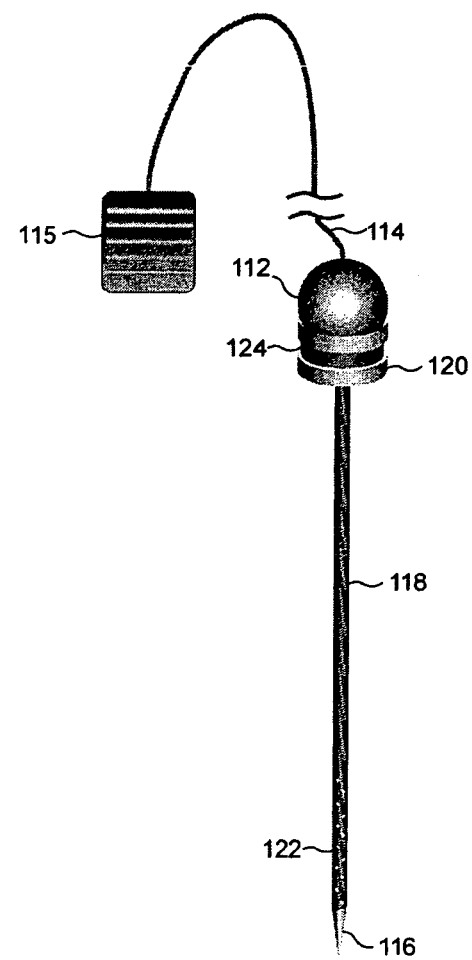
FIG. 3B is a isometric view of the trocar obturator unit and catheter assembly in accordance with another embodiment of the present invention, shown as assembled.

As device 100 is assembled prior to its use, stylet 110 is removably retained in catheter assembly 104, as shown in FIGS. 2B and 2C. In a preferred embodiment, as shown in FIG. 2A, stopper 112 is a cylindrically-shaped component with a planar bottom surface that rests flush on the interior bottom wall of hub 120. The upper portion of stopper 112 tapers inward towards pull-handle 114. In another preferred embodiment, as shown in FIG. 3A, stopper 112 is a sphere integrally attached to stylet 110. In this embodiment, when stylet 110 is fully inserted into tube 118, as shown in FIG. 3B, stopper 112 engages hub 120, such that at least a lower portion of the sphere rests within the central opening of hub 120. In this embodiment, the upper surface of annular rim 128 slopes downwards to accommodate the spherical curvature of stopper 112, such that stopper 112 rests securely upon hub 120. In both embodiments, catheter assembly 104 and trocar obturator unit 102 are dimensioned such that point 116 extends beyond the most proximal end of catheter tube 118 when trocar obturator unit 102 is fully inserted into catheter assembly 104 and stopper 112 engages hub 120. The aforementioned tapered and spherical designs of stopper 112 facilitate the easy removal of trocar obturator unit 102 from catheter assembly 104 without tearing one-way valve 106.

Figure 4:
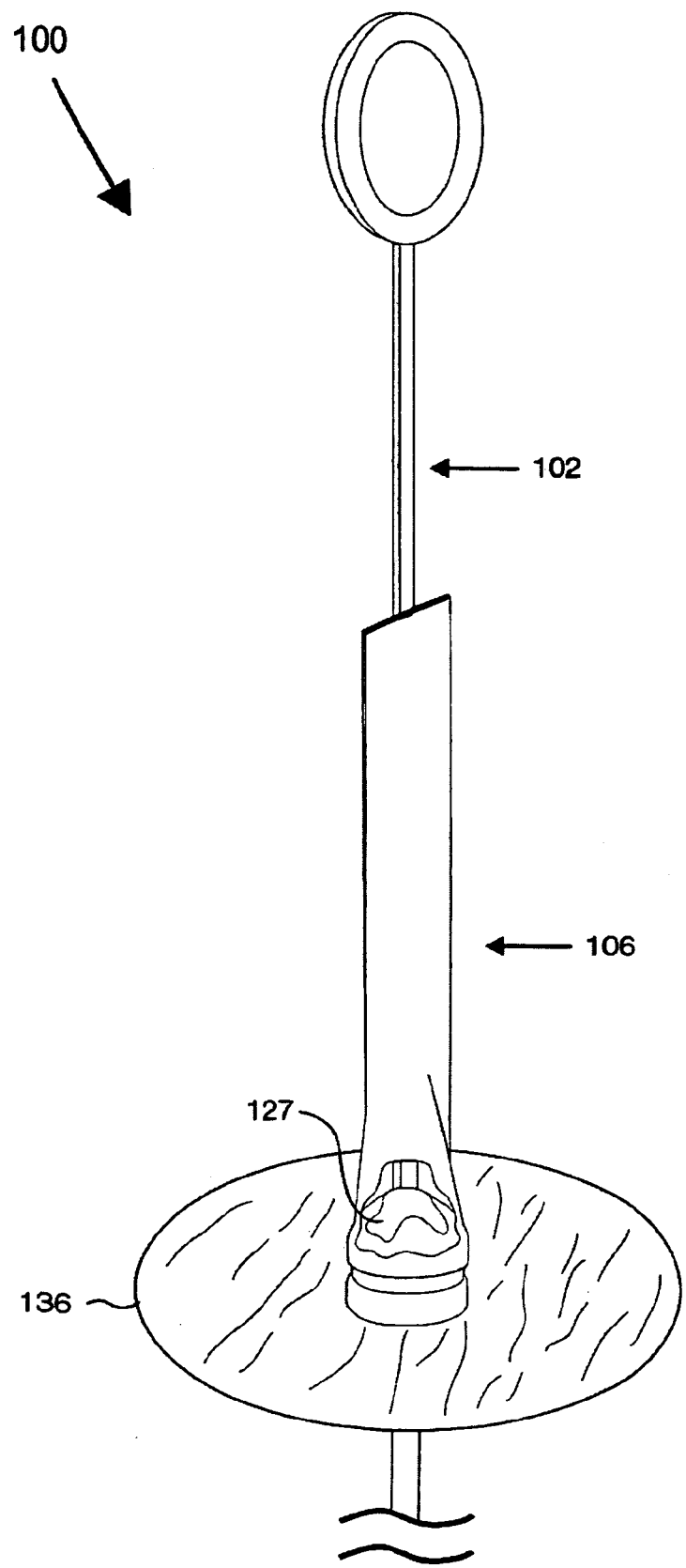
FIG. 4 is a partial prospective view of the pneumothorax and/or hemothorax treatment device in accordance with one embodiment of the present invention, showing a cut-away view of the one-way valve.

During the manufacture of device 100, stopper 112 may be coated with a water-based, bateriostatic, glycerin lubricant such as Surgilube™, or K-Y® Brand Lubricating Jelly prior to covering hub 120 and trocar obturator with one-way valve 104, as shown in FIG. 4.

The entire trocar obturator unit 102, as well as the catheter assembly 104 including the catheter tube 118 and hub 120 are preferably composed of radio-opaque material, or contain radio-opaque markers. By using radio-opaque material one can ascertain not only the path which the catheter tube has taken when inserted, but also provides a means for determining the position of the catheter assembly 104 after it has been employed in the patient. Thus, the radio-opaque material delineates on X-ray film, for example, the catheter tube's position relative to the patient's chest wall and within the pleural space. Use of radio-opaque markers for catheter placement and position in any body cavity or lumen is well known and established by those with skill in the profession.

Figure 5:
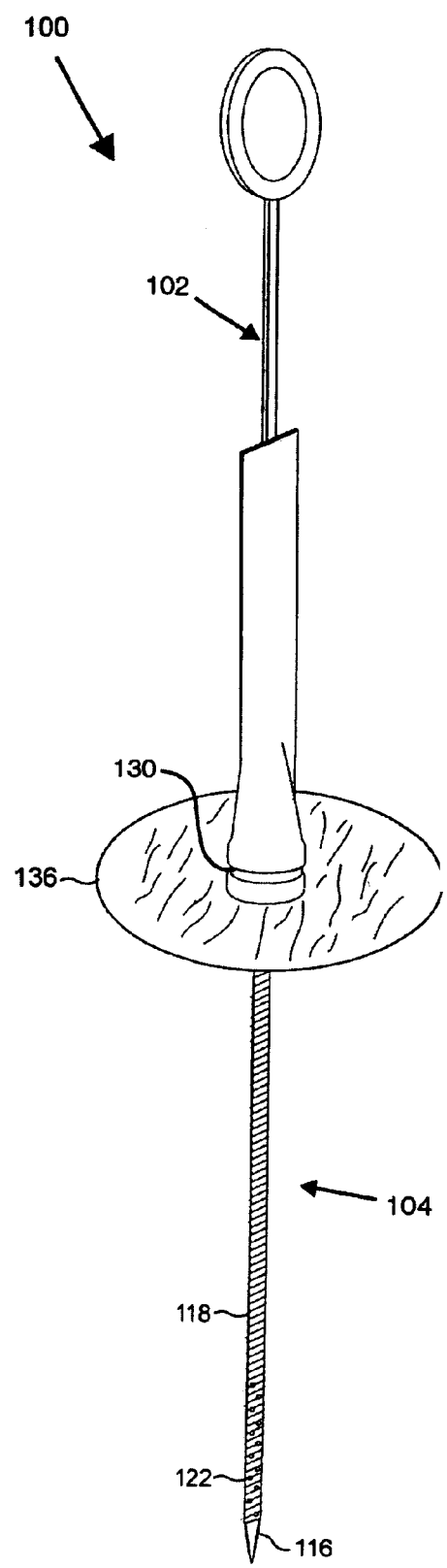
FIG. 5 is a isometric view of the pneumothorax and/or hemothorax treatment device in accordance with one embodiment of the present invention.
Figure 7:
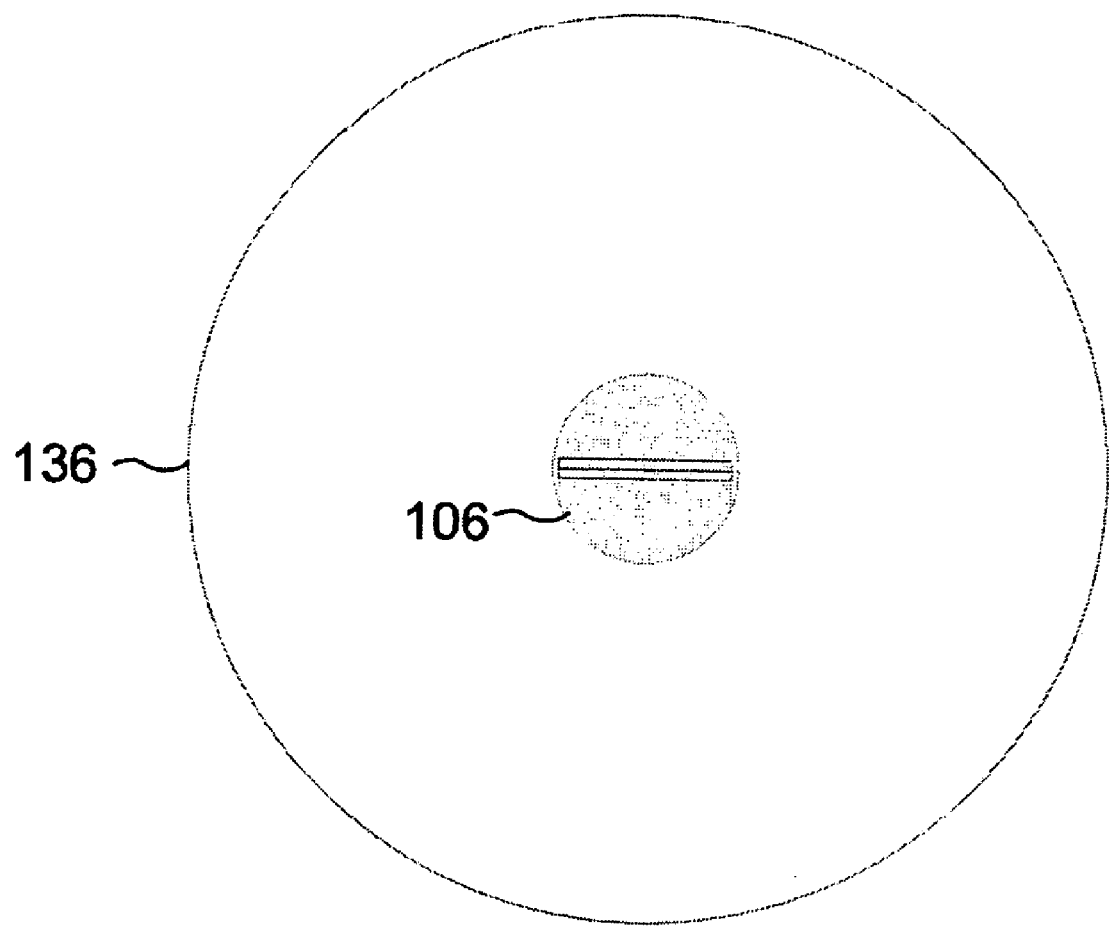
FIG. 7 is a plane view of the one-way valve and disk of the pneumothorax and/or hemothorax treatment device, in accordance with one embodiment of the present invention.

Referring again to FIGS. 1 and 2C, one end of one-way valve 106 extends over and covers hub 120. One-way valve 106 is preferably a Heimlich-type valve constructed of pliable material, e.g. latex or natural rubber, capable of tightly engaging hub 120 so as to be securely retained thereon. During periods of non-use, the sides of one-way valve 106 are biased together as a function of its elasticity, as shown in FIG. 7. As discussed below, when treating a pneumothorax and/or hemothorax, the air released from the chest cavity, for example, travels upwards through tube 118 and into one-way valve 106. The force of the expelled air forces the sides of one-way valve 106 to separate, allowing the air to exit the one-way valve 106 at its distal end. As the air is released from one-way valve 106, the sides of one-way valve against collapse against each other. A retaining ring 130, as shown in FIG. 5, is dimensioned to fit within the recess 124 may be used to secure one-way valve to hub 120, in an airtight fashion, and so as to ensure that one-way valve will not be unintentionally disengaged from hub 120 when trocar obturator unit 102 is removed through the lumen of the one-way valve 106.

Pull-handle 114 extends through the lumen of and out the distal opening of one-way valve 106 so that the grasping portion 115 of pull-handle 114 is accessible. The grasping portion 115 of pull-handle 114 is preferably a plastic ring, as illustrated in FIG. 1, or a tab connected to a string 115, as illustrated, for example in FIG. 3. In the most preferred embodiment, however, the entire trocar orbturator unit 102, including pull-handle 114 is fabricated of a single piece of high-strength plastic, polymer, metal, or other material.

In a preferred embodiment, as a means to secure the device to the patient is at least one band 132 integrally attached to at least one adhesive coated tab 134. Adhesive tabs 134 are coated with any known type of medical skin adhesive such as such as 3M™ Acrylate Polymer®. Bands 132 are preferably wound around recess 124 in a manner that each adhesive coated tab 134 can be pulled to opposing sides of hub 122. There are preferably at least two adhesive-coated tabs 134. The ends of bands 132 to which adhesive tabs 134 are not attached are anchored to the hub in the same recess 124 as the retaining ring 130. As assembled prior to use, the full-length of band 132 may be stored within recess 124.

Adhesive tabs 134 are continuous with and made of the same material as bands 132, and are preferably made of a thin flexible, polymeric material such as Tyvek®, 3M™ polyethylene film, or other similar plastic. Only one side of adhesive bands 132 are coated with adhesive. A thin, removable plastic film (not shown) covers the adhesive-coated side of adhesive-coated bands 132 to preserve the nature of the adhesive and to prevent it from becoming contaminated, generally, during non-use. This thin plastic film which covers the adhesive-coated band 132 can be any of the known type capable of being quickly and easily removed from the adhesive layer without sacrificing the usefulness of and adhesive qualities of the adhesive.

In another preferred embodiment, provided as an another means of securing device 100 to the patient is a disk 136, as shown in FIG. 5. Disk 136 has an centrally positioned aperture (not shown) for receiving hub 120 and is permanently and integrally fixed to the bottom (proximal) end of hub 120 in the manufacturing process. Disk 136 is constructed of a pliable, thin, flexible material such as 3M™ polyethylene film, 3M™ Tegaderm,™ or Tyvek® that is conformable to accommodate the various contours of the human body, especially the female breast or a well-developed male chest. The proximal side of disk 136 is coated with any known type of medical skin adhesive such as 3M™ Acrylate Polymer® or the like. Similar to adhesive tabs 134, thin, removable paper or plastic film (not shown) covers the adhesive-coated side of disk 136 to preserve the nature of the adhesive and to prevent it from becoming contaminated, generally, during non-use.

Figure 6:
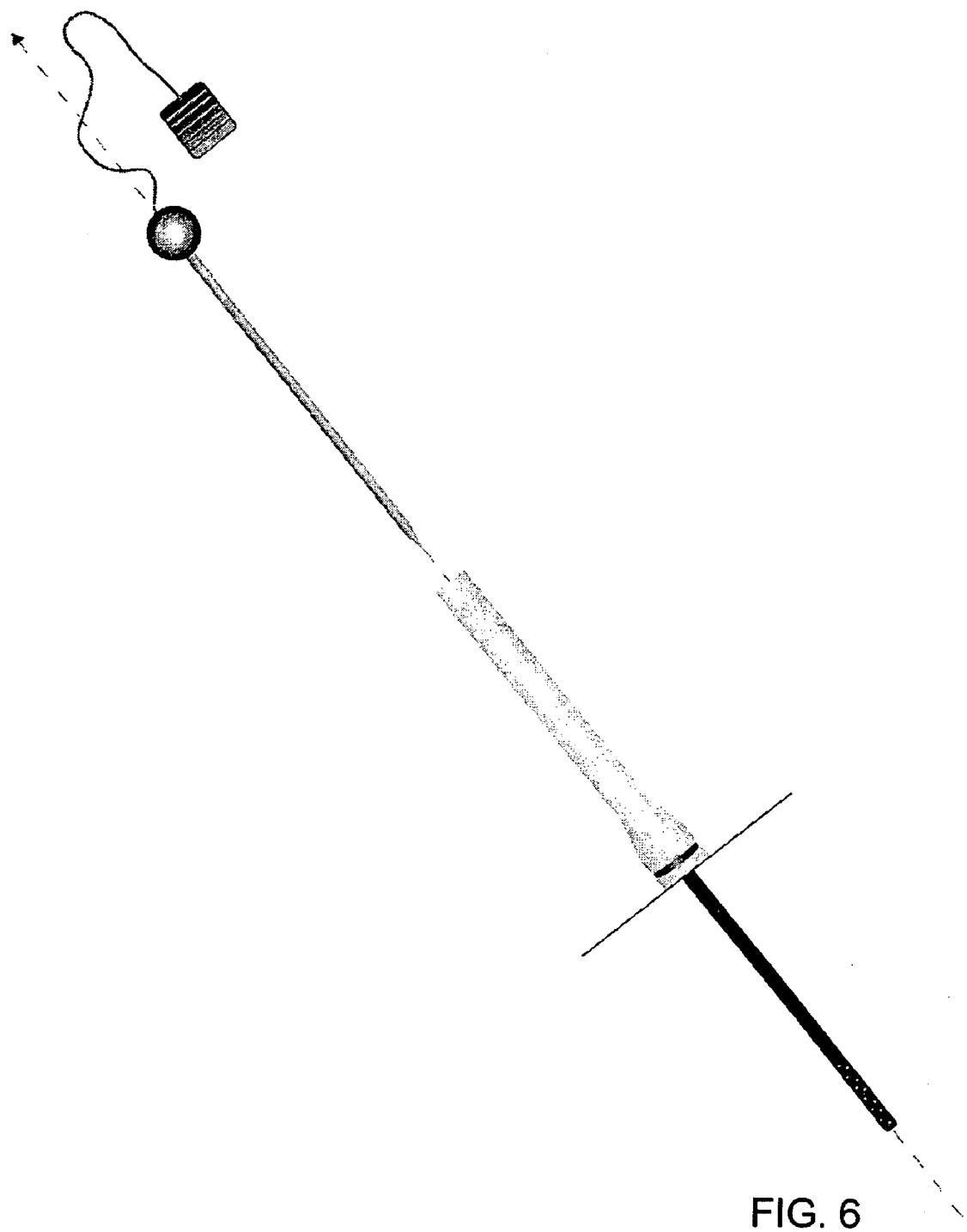
FIG. 6 is a isometric view of the pneumothorax and/or hemothorax treatment device in accordance with one embodiment of the present invention, depicting the manner in which the trocar obturator is removed from the catheter assembly and one-way valve.

To use device 100 in a patient suspected of having a tension pneumothorax, and/or hemothorax, the patient's chest is exposed, and cleaned of all sweat, blood, and other debris. If time permits, antimicrobial solution such as povidone iodine or chlorhexidine gluconate solutions are applied to the area in the usual fashion. The Applicant's device is removed from its individual sterile packaging. The point 116 of stylet 110 is sharply inserted into and through the chest wall in the second intercostal space, in the mid-clavicular line (an imaginary line drawn straight down from the middle of the clavicle), on the ipsilateral side as the suspected pneumothorax, until the proximal side of the hub 120 is resting on the patient's skin. This is the accepted location for venting of a tension pneumothorax. The grasping portion 115 of pull-handle 114 is grasped and pulled, thereby causing the trocar obturator 102 to slide distally out of the one-way valve 106, as illustrated in FIG. 6. The glycerin-based lubricant 127 allows the trocar obturator unit to easily slide through one-way valve 106. The trocar obturator is then disposed of in an appropriate sharp-waste container. At the moment the trocar obturator is withdrawn from one-way valve 106, excess pressure and/or blood from inside the patient chest cavity is allowed to escape through one-way valve 106, thereby relieving the tension pneumothorax and/or hemothorax. As the patient exhales, the exhaled air travels through tube 118 of catheter assembly 104 and into the lumen of one-way valve 106. The pressure of the exhaled air separates the sides of the one-way valve 106, allowing the air to escape therethrough. After the exhaled air is expelled through the distal end of one-way valve 106 and the patient inspires, the sides of one-way valve 106 collapse back against each other, thus preventing air, environmental contaminants, and/or blood from returning through one-way valve 106.

Once the pneumothorax and/or hemothorax is released, device 100 can be affixed to the patient. To do so, bands 132, for example, are unwound from recess 124 to the extent necessary for the adhesive bands 132 to reach the point of desired attachment on the patient. The protective film is removed from the adhesive-coated tabs 134 or from the adhesive coated disk 136. The adhesive side of adhesive-coated bands 132 or the adhesive side of the disk 136 is then affixed to the patient's body so as to stabilize the position of the pneumothorax treatment device on the patient. Alternatively, tabs 132 or disk 136 could be stapled to the skin by methods known to those with skill in the profession.

Device 100 is specially designed to immediately relieve tension pneumothorax, and/or hemothorax in the chest cavity of animals, particularly humans. A primary advantage of the present invention is that it can be used by pre-hospital personnel, such as emergency medical technicians and the like, or hospital personnel, with minimal training, as well as by physicians and more experienced medical professionals. Device 100 allows for the treatment of a pneumothorax, tension pneumothorax, tension pneumothorax, and/or hemothorax without requiring the assembly of parts, or connection to auxiliary devices. Device 100 provides another particularly unique advantage over currently used pre-hospital treatment methods for tension pneumothorax in that because of its one-way valve design it minimizes or prevents chemical, biological, and radiological contamination into the chest cavity when used in battlefield or warfighting situations. The current method of using a 14 gauge intravenous catheter causes open communication with the ambient air, including all airborne battlefield contaminants. Accordingly, device 100 is particularly well-suited for use in treating pneumothorax, tension pneumothorax, and/or hemothorax on a battlefield or in mass-trauma situations. The compact size of the device enables medical personnel to carry a relatively large number of these devices in small portable medical kits or within their garment pockets. The associated time savings of not having to assemble the device prior to use, carry large cases of unassembled components, and frequently return to medical storage houses or trucks to obtain an additional supply of the devices, is invaluable, as pneumothorax, tension pneumothorax, and hemothorax are very serious medical conditions, which if not promptly treated, are likely to cause serious systemic injuries, cardiovascular compromise, and death.

Another advantage offered by the present invention is its ability to be quickly affixed to the skin of a patient in a manner superior to known needle-thoracostomy devices and like devices, thereby freeing the hands of the treating physician or medical personnel. This ability to securely affix the device to the patient also enables the patient to be transported without the device becoming dislocated or dislodged from the patient's chest. When treating patients suffering from a pneumothorax, tension pneumothorax and/or hemothorax on a battlefield, therefore, the ability to quickly affix the device to the patient also allows the treating medical personnel to evacuate from an area of potential danger.

The kink-resistant tubing 118 also offers a significant advantage over conventional devices. With conventional devices, for example, it is common for the catheter tubing to kink, unless the caregiver is careful to hold the catheter upright at all times. Kinking also commonly occurs when blankets are placed over a catheter in order to maintain the patient's body temperature. In the present invention, the kink-resistant nature of the specialized catheter tubing 118 frees the caregivers hands, thereby allowing the caregiver to transport the patient and tend to others.

From the foregoing, it can be seen that the present invention provides a simple, inexpensive, and yet totally effective means for treating pneumothorax, tension pneumothorax, and/or hemothorax within animals, especially humans. Moreover, it should also be apparent that device 100 can be made in varying lengths and sizes to treat both adults, children, and infants.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A device for treating pneumothorax, tension pneumothorax, and/or hemothorax, comprising:
    a trocar obturator unit comprising a stylet with a distal end and a proximal end, wherein the proximal end of said stylet has a point for puncturing a body cavity, and wherein a stopper is coupled to said stylet distally of said point;
    a catheter assembly comprising
        a tube dimensioned to receive said stylet, said tube having a lumen, an open ended distal end portion, and at least one fluid opening through the sidewall, and
        a hub coupled with said open-ended distal end portion, wherein a lumen of said hub is continuous with the lumen of said tube and dimensioned to receive at least a portion of said stopper to position the stylet relative to the catheter assembly and seal the lumens of said tube;
    a one-way valve, wherein one end of said one-way valve is sealed to at least a portion of said hub, said one-way valve being configured such that the lumen of the one-way valve is continuous with the lumens of said tube and said hub;
    an at least one band having a first end and a second end, the first end coupled to the hub; and
    an at least one adhesively coated tab attached to the at least one band, the at least one adhesively coated tab attachable to a portion of skin near the body cavity to mechanically affix the catheter assembly to the skin.

2. The device of claim 1, wherein the point on the proximal end of said stylet extends beyond the proximal end portion of said tube when said stylet is inserted into said catheter assembly.

3. The device of claim 1, wherein the diameter of said stopper is larger than the diameter of the lumen of said one-way valve.

4. The device of claim 1, wherein at least a portion of said stopper is removably retainable in at least a portion of the hub.

5. The device of claim 1, wherein at least one of the exterior of said stopper or the interior of said one-way valve is coated with a lubricant.

6. The device of claim 1, wherein said trocar obturator unit further comprises a pull-handle attached to said stopper.

7. The device of claim 6, wherein said pull-handle is a ring.

8. The device of claim 6, wherein said pull-handle is a tab.

9. The device of claim 1, wherein an annular recess is formed in the outside wall of said hub.

10. The device of claim 1, wherein said one-way valve is secured to said hub by a retaining ring position over said one-way valve within said recess.

11. The device of claim 9 wherein said one-way valve is secured to said hub by the at least one band unwindably positioned over said one-way valve within the recess of said hub.

12. The device of claim 11 wherein said at least one tab includes a removable covering for maintaining said adhesive during periods of non-use.

13. The device of claim 1, further comprising a disk coupled to said catheter assembly for securing said trocar unit to a patient.

14. The device of claim 6, wherein at least one of said stylet, catheter assembly, one-way valve and pull-handle are comprised of a radio-opaque material.

15. The device of claim 1, wherein said tube includes a kink-resistant tube lumen wall.

16. The device of claim 1, wherein said the kink-resistant lumen wall includes a first coiled monofilament polymer fiber.

17. The device of claim 16, wherein the kink-resistant lumen wall includes a second coiled monofilament polymer fiber interwoven with the first coiled monofilament polymer fiber.

18. The device of claim 15 wherein the kink-resistant lumen wall includes a coiled monofilament metallic fiber.

19. The device of claim 16, wherein the kink-resistant lumen wall includes a second coiled monofilament metallic fiber interwoven with the first coiled monofilament metallic fiber.

20. A catheter assembly for venting fluid including gasses from within a body cavity having a skin, the catheter assembly comprising:
    a tube configured to sealingly engage a stylet, the tube having a tube lumen, a tube distal end defining a tube distal port, and a tube proximal end defining a tube proximal port;
    a hub defining a hub lumen, the hub having a hub proximal face, a hub distal face, and the hub proximal face being sealingly attached to the tube at the tube distal port, the hub lumen configured to form a passage for fluid continuous with the tube lumen and dimensioned to receive at least a portion of a stopper on a stylet, in sealing engagement with the tube lumen;
    an at least one band having a first end and a second end, the first end coupled to the hub;
    an at least one adhesive film-coated tab attached to the at least one band, the at least one adhesive film-coated tab attachable to a portion of the skin near the body cavity to cause the hub proximal face to be substantially seated against the skin; and
    a one-way valve, in sealing engagement with the hub distal face, the one-way valve being configured such that a one-way valve lumen is continuous the passage the hub lumen and the tube lumen form.

21. The catheter assembly of claim 20, the assembly further comprising:
    a trocar obturator unit including the stylet having a stylet distal end and a stylet proximal end, wherein the proximal end of said stylet having a point for puncturing a body cavity, and wherein a stopper is coupled to said stylet distally of said point, the stopper being configured to position the stylet relative to the catheter assembly.

22. The catheter assembly of claim 21, wherein the point is a suitable length to extend beyond the tube proximal port when the stylet is inserted into the tube to bring the stopper into engagement with the hub.

23. The catheter assembly of claim 21, wherein the diameter of the stopper is larger than the diameter of the one-way valve lumen.

24. The catheter assembly of claim 21, wherein the trocar obturator unit further includes a pull-handle attached to the stopper.

25. The catheter assembly of claim 24, wherein the pull-handle includes a ring.

26. The catheter assembly of claim 24, wherein the pull-handle includes a tab.

27. The catheter assembly of claim 20, wherein the hub proximal face defines an annular recess.

28. The catheter assembly of claim 20, further comprising:
an adhesive coated disk coupled to the hub.

29. The catheter assembly of claim 20, wherein said at least one tab includes a removable covering for maintaining said adhesive during periods of non-use.

30. The catheter assembly of claim 20, wherein at least one of the group consisting of the stylet, the tube, the hub, the one-way valve, and the pull-handle comprise a radio-opaque material.

31. The catheter assembly of claim 20, wherein the tube-includes a kink-resistant tube lumen wall.

32. The catheter assembly of claim 20, wherein said the kink-resistant lumen wall includes a first coiled monofilament fiber.

33. The catheter assembly of claim 32, wherein the kink-resistant lumen wall includes a second coiled monofilament fiber interwoven with the first coiled monofilament polymer fiber.

34. The catheter assembly of claim 32, wherein the fiber includes a polymer fiber.

35. The catheter assembly of claim 32, wherein the fiber includes a metallic fiber.

36. The catheter assembly of claim 35, wherein the metallic fiber includes stainless steel.

37. The device of claim 1, wherein the at least one band includes one side coated with an adhesive material.

38. The device of claim 1, wherein the at least one adhesively coated tab is attached to the second end of the at least one band.

39. The device of claim 1, wherein the second end of the at least one band is unwindable from the hub to extend tangentially from the hub.

40. The device of claim 39, wherein the at least one band remains wound around the hub until after the stylet has entered the body cavity.

41. The device of claim 1, wherein the hub includes an annular recess.

42. The device of claim 41, wherein the second end of the at least one band is unwindable from the recess to extend tangentially from the recess.

43. The device of claim 1, wherein the at least one adhesively coated tab maintains the catheter assembly in an operative posture without assistance from medical personnel after the at least one adhesively coated tab is attached to the portion of skin.

44. The device of claim 1, wherein the at least one band is flexible.

45. The catheter assembly of claim 20, wherein the at least one adhesive film-coated tab is attached to the second end of the at least one band.

46. The catheter assembly of claim 20, wherein the second end of the at least one band is unwindable from the hub to extend tangentially from the hub.

47. The device of claim 27, wherein the second end of the at least one band is unwindable from the annular recess of the hub to extend tangentially from the annular recess.

48. The device of claim 20, wherein the at least one adhesive film-coated tab maintains the catheter assembly in an operative posture without assistance from medical personnel after the at least one adhesive film-coated tab is attached to the portion of skin.

49. The device of claim 20, wherein the at least one band is flexible.

* * * * *

UNITED STATES PATENT AND TRADEMARK OFFICE
CERTIFICATE OF CORRECTION

PATENT NO. : 7,229,433 B2
APPLICATION NO. : 10/656245
DATED : June 12, 2007
INVENTOR(S) : Gary J. Mullen It is certified that error appears in the above-identified patent and that said Letters Patent is hereby corrected as shown below:

Title Page, item [76] Inventor's correct spelling is: -- Gary J. Mullen --

Signed and Sealed this

Twenty-third Day of October, 2007

JON W. DUDAS
*Director of the United States Patent and Trademark Office*